US005629203A

United States Patent [19]

Shuster

[11] Patent Number: 5,629,203
[45] Date of Patent: May 13, 1997

[54] METHOD FOR INTEGRATIVE TRANSFORMATION OF YEAST USING DISPERSED REPETITIVE ELEMENTS

[75] Inventor: Jeffrey R. Shuster, Fairfield, Calif.

[73] Assignee: Chiron Corporation, Emeryville, Calif.

[21] Appl. No.: 346,836

[22] Filed: Nov. 30, 1994

Related U.S. Application Data

[63] Continuation of Ser. No. 990,352, Dec. 15, 1992, abandoned, which is a continuation of Ser. No. 556,221, Jul. 20, 1990, abandoned.

[51] Int. Cl.$^6$ .......................... C12N 15/00; C12N 15/09; C12N 15/63; C12N 15/81
[52] U.S. Cl. .......................... 435/320.1; 435/6; 435/69.6; 435/172.3; 536/24.1; 536/24.2; 935/28; 935/55; 935/68; 935/69
[58] Field of Search .......................... 536/24.1, 24.2; 435/69.6, 320.1, 6, 172.3; 935/68, 69, 55, 28

[56] References Cited

FOREIGN PATENT DOCUMENTS 8803169  5/1988  European Pat. Off. .......... C12N 1/18

OTHER PUBLICATIONS

Cameron et al., (1979) *Cell* 16:739–751.
Futcher et al., (1984 *Journal of Bacteriology* 157:283–290.
Karin et al., (1984) *Proc. Natl. Acad. Sci.* 81: 337–341.
Lopes et al., (1989) *Gene* 79:199–206.
Orr–Weaver et al., (1983) *Methods in Enzymology* 101:228–245.
Smith et al., (1985) *Science* 229:1219–1224.
Warmington et al., (1985) *Nucleic Acids Research* 13(18):6679–6693.
Cousins et al, Gene 61:265–275 (1987)"High Level Expression of Proinsulin in yeast, *S. cerevesiae*".
Warmington et al, Nucleic Acids Research 13:6679 Nucleotide Sequence Characterization of Tyl–17, a Class II Transposon.
Lopes et al, Gene 79: 199–206 (1989) High Copy Number Integration into the Vibosomal DNA of *S. cerevesiae*.
Karin, PNAS 81:337–341 (1984) Primary Structure ... CUP 1 Locus.

Primary Examiner—Mindy Fleisher
Assistant Examiner—Bonnie D. Weiss
Attorney, Agent, or Firm—Roberta L. Robins; Kenneth Barovsky; Robert P. Blackburn

[57] ABSTRACT

Efficient integration of heterologous DNA into yeast genomic DNA is accomplished at high copy number by targeting integration vectors to dispersed repetitive elements such as DELTA sequences, Ty elements, or tRNA DNA sequences present in the host cell genome.

20 Claims, 5 Drawing Sheets

METHOD FOR INTEGRATIVE TRANSFORMATION OF YEAST USING DISPERSED REPETITIVE ELEMENTS

This application is a continuation of application Ser. No. 07/990,352 filed on 15 Dec. 1992, now abandoned, which is a continuation of abandoned application Ser. No. 07/556,221, filed on 20 Jul. 1990.

DESCRIPTION

1. Technical Field

This invention relates to the molecular biology of yeast and fungi, and to methods for transforming yeast with integrative plasmids.

2. Background of the Invention

Recombinant protein expression is currently practiced using a variety of expression systems and host cells, each having its own advantages and disadvantages. Prokaryotes such as *E. coli* are often employed because *E. coli* strains are well characterized, several strong promoters are available, the host cells support a large number of plasmids convenient for transformation and expression, and the host cells may be grown to high densities relatively easily. However, prokaryotic hosts are incapable of correctly expressing products from DNA containing introns, and do not generally provide for protein glycosylation, which may be required for activity and/or stability in many eukaryotic proteins.

Mammalian cells, such as CHO and COS cells are sometimes used for protein expression. Mammalian cells can express products from DNA containing introns, and are generally able to express proteins having the proper glycosylation, disulfide bonding, etc. However, mammalian cells are often very difficult to culture, and are susceptible to infection. They are also substantially more complex, and may require that the heterologous DNA be integrated into the host cell genome, sometimes with unpredictable results.

Yeast strains have proven to be particularly good for expressing heterologous proteins. Unlike *E. coli* and mammalian cells, many yeasts are not susceptible to viral infection. There are a variety of suitable genera, such as Saccharomyces, Schizosaccharomyces, Kluveromyces, Pichia, Hansenula, and the like, as well as a number of useful expression plasmids. Techniques for culturing yeast are well established. However, it has been found that autonomously-replicating plasmids in yeast are often subject to instability, resulting in loss of the plasmid after a number of generations. See e.g., A. B. Futcher et al., *J. Bacteriol,* (1984) 157:283–90. Alternatively, one may transform the yeast with a vector designed to integrate into the yeast genome. However, one must provide a vector having homology to a particular site within the yeast genome to obtain integration at any useful frequency. The homology requirement is a severe restriction, because it limits the usefulness of an integrating vector to integration at only one site (or at most, generally 2–3), and to use with only one variety of yeast (having genomic DNA homologous to the targeting sequence). Thus, introduction of a heterologous gene at a high copy number requires either a large number of individually-targeted vectors, or targeting to one highly-repetitious sequence such as the tandemly repeated ribosomal DNA region.

T. L. Orr-Weaver et al., *Meth. Enzymol.* (1983) 101:228–45 reported construction of integrating plasmids having DNA homologous to a yeast gene. By introducing a double-strand break in the yeast-homologous region of the plasmid, Orr-Weaver was able to increase transformation frequency up to 3000-fold, depending upon the homologous gene selected.

R. A. Smith et al., *Science* (1985) 229:1219–24 compared expression of calf prochymosin in yeast from plasmid vectors and integrated vectors. Smith found that expression from integrated DNA produced about four times the amount of active enzyme obtained from plasmid expression, even where the plasmid copy number was about 100/cell. Integration at four sites in the yeast genome resulted in a three-fold increase in secreted active enzyme.

T. S. Lopes et al., *Gene* (1989) 79:199–206 disclosed yeast integration vectors targeted to the ribosomal DNA (RDNA), which is present in the genome in about 140 copies repeated in tandem. Lopes et al. constructed integration vectors having several Kb of yeast RDNA, Leu2-d (for selection), and either phosphoglycerate kinase (PGK) or Mn-dependent superoxide dismutase (Mn-SOD). Targeting to the genomic RDNA site was accomplished by cleaving within the RDNA region of the vector. However, although the vectors apparently integrated in 100+copies at the RDNA site, and provided increased expression of PGK and Mn-SOD, the authors were unable to obtain high-copy integration using marker genes other than Leu2-d.

Disclosure of the Invention

The present invention comprises integrating plasmid vectors capable of inserting heterologous DNA sequences dispersed throughout the yeast genome with high copy number, and methods for providing heterologous integration at dispersed locations. The vectors and methods employ dispersed repetitive elements (DRE's) in the yeast genome, such as the yeast DELTA sequences, for integration target sequences.

Modes of Carrying Out the Invention

A. Definitions

Figure 1:
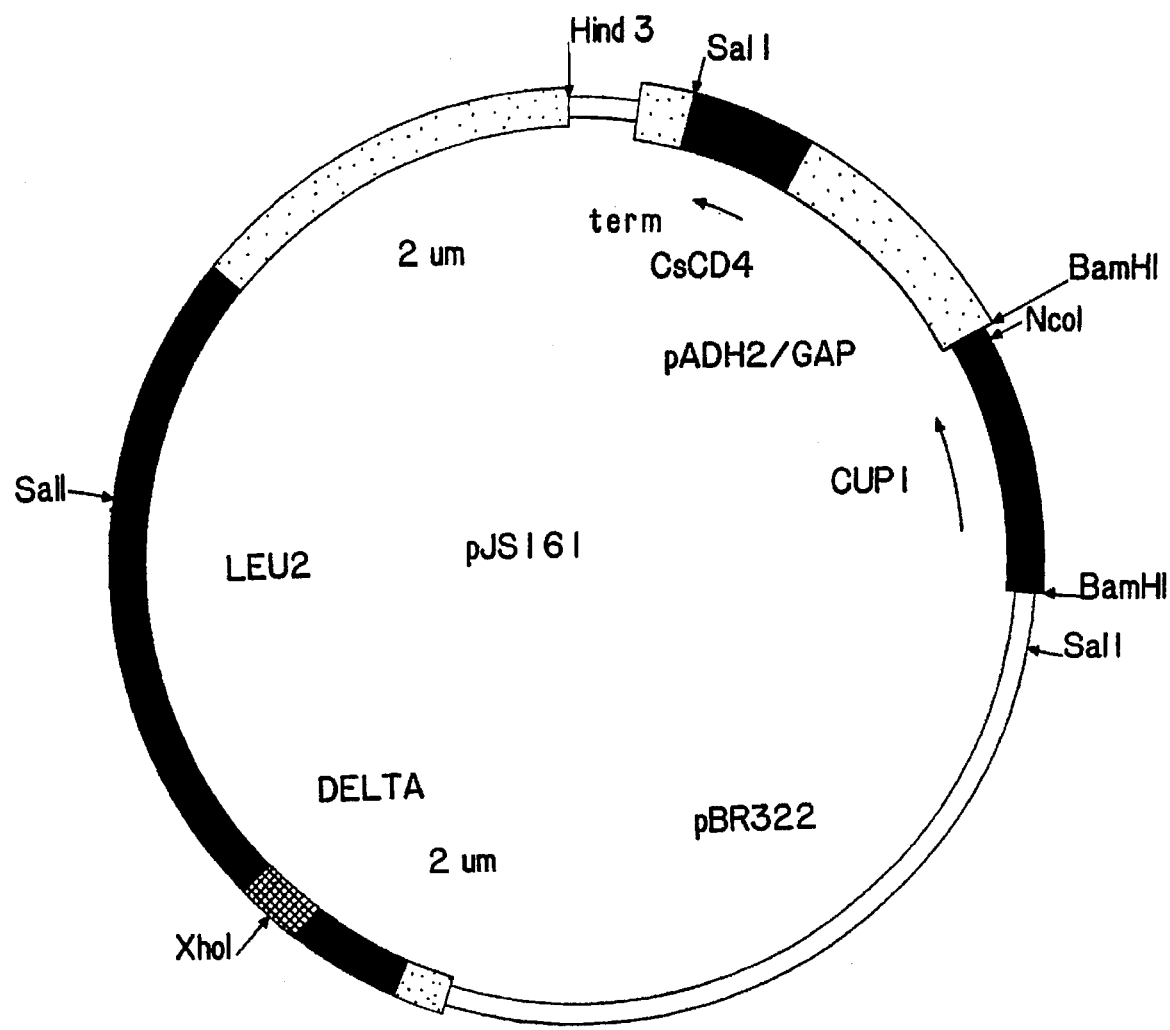
FIG. 1 depicts a map of plasmid pJS161.

The term "dispersed repetitive element" refers to a DNA sequence found in multiple locations within the yeast genome (i.e., within the chromosomes), wherein each occurrence of the element is substantially homologous to the other elements. Dispersed repetitive elements within the scope of this invention occur in at least two copies within the genome, preferably at least about 5 copies, and more preferably about 20–300 copies. The copies need not be identical, but should be homologous to a degree sufficient to permit integration at each copy. These repetitive elements must also be dispersed, i.e., they do not usually occur in tandem or adjacent repeats, but are usually separated by at least about 300–500 bases. Exemplary dispersed repetitive elements are DELTA sequences, Ty sequences, and tRNA DNA sequences.

The term "target sequence" refers to a site within the genome of a yeast host cell at which integration is intended to occur. In the present invention, target sequences are dispersed repetitive elements.

The term "targeting sequence" refers to a DNA sequence homologous to the selected dispersed repetitive elements in the yeast host genome, which is capable of directing integration at the dispersed repetitive elements. The targeting sequences will have at least the minimum length necessary for efficient integration, generally at least about 50 bp, more preferably about 100 bp, and most preferably 100–200 bp. The targeting sequences must also be sufficiently homologous to the selected dispersed repetitive elements to insure integration at multiple sites: the targeting sequences need not be identical to any particular individual site, but preferably resemble a "consensus sequence" of target sites.

The term "heterologous DNA" as used herein refers to any DNA that is inserted in a non-native state. For example, DNA encoding mammalian or prokaryotic proteins (e.g., epidermal growth factor, insulin-like growth factors, glucose oxidase, and the like) is considered "heterologous" within this definition. Further, proteins normally found in yeast may be heterologous within the scope of the invention if the structural gene is associated with a different promoter or terminator sequence, if the protein coding sequence is altered (whether or not the encoded amino acid sequence is changed), if the protein is not normally found in the particular yeast host selected, if the gene is introduced at amplified levels greater than the levels found in wild-type yeast, and so forth. A structural gene is in "operable association" with a promoter and/or terminator if the promoter and/or terminator function in the integrated construct to control or modulate expression of the structural gene.

The term "unique restriction endonuclease recognition site" refers to a DNA sequence which is recognized and cleaved by a selected restriction endonuclease, and which is present in only one occurrence within the DNA molecule. If desired, one may employ vectors having more than one copy of the restriction endonuclease recognition site if the other sites are protected, e.g., by methylation. Thus, the vectors of the invention require that the targeting sequences flank a restriction endonuclease recognition site which is uniquely susceptible to cleavage, whether the same sequence occurs elsewhere in the molecule or not. Alternatively, it is possible to have more than one copy of the restriction endonuclease recognition site in a plasmid to be cleaved and to generate linear molecules by partial digestion of the plasmid with the appropriate enzyme.

The term "selectable marker" refers to a DNA sequence which permits identification and/or segregation of transformants bearing that sequence. It is generally preferred to employ selectable markers which confer improved survival for the host, for example by conferring antibiotic resistance, metal ion resistance, prototrophy for a given nutrient, and the like. Successfully transformed host cells may then be separated from non-transformants by culturing the yeast under selective conditions, for example by growing the yeast in the presence of antibiotics or metal ions, or by growing the yeast in a medium deficient in an essential nutrient. Other markers include genes for luminescent proteins, well-defined antigens, and unique DNA sequences detectable by probe.

B. General Method

There are a number of dispersed repetitive elements found within the yeast genome. The prime examples are DELTA elements, Ty transposons, centromeres, telomeres, and tRNA DNA. The presently preferred dispersed repetitive elements are DELTA elements. See e.g., J. R. Cameron et al., *Cell* (1979) 16:739–51; and J. R. Warmington et al., *Nucl. Acids Res.* (1985) 13:6679–93. As the nucleotide sequences are reported in the literature, one may easily construct multiple site-directed recombinant vectors based on these sequences.

The vectors of the invention will in general be linear dsDNA molecules having an expression cassette and targeting sequences at the 5' and 3' ends of the molecule. Alternatively, the vectors may be provided in the form of circular plasmids having a unique restriction endonuclease recognition sequence positioned so that a linear dsDNA vector of the invention is obtained following digestion. The vectors may further include selectable markers, preferably situated between the targeting sequences and the expression cassette. The expression cassette will in general include a promoter, a structural gene, and a terminator sequence, linked to provide expression of the structural gene. The promoter is preferably inducible. One may additionally include signal sequences, such as yeast α-factor, to provide for secretion of the expressed protein. The expression cassette may include more than one structural gene, and the vector may include more than one expression cassette.

The structural gene may encode any protein, polypeptide, or RNA product, whether eukaryotic or prokaryotic in origin, and may or may not contain introns. For reasons of integration efficiency, it is preferred to limit the size of the structural gene to no more than about 50 Kb, more preferably about 10 Kb, and most preferably $\leq$1 Kb. The gene product should also be relatively nontoxic to the selected host in the form in which it is expressed (i.e., a toxic protein may be expressed in an unactivated form, or in a form which is not toxic enough to prevent yeast growth). Exemplary structural genes encode polypeptide growth factors such as epidermal growth factor (EGF), insulin-like growth factors (IGFs), human growth hormone (hGH), growth hormone releasing factor (GRF), interleukin-1α (IL-1α), IL-1β, IL-2, transforming growth factor-α (TGF-α), TGF-βs, fibroblast growth factor (FGF), Connective Tissue Activating Peptides (CTAP-I, CTAP-II, CTAP-III), and the like; receptors such as human CD4 receptor, EGF receptor, TGF-β receptor, GH receptor, estrogen receptor, and the like; antigens, such as Human Immunodeficiency virus (HIV) gp120, Herpes Simplex Virus (HSV, type I and/or type II) gB and gD, *Chlamydia trachomatis* major outer membrane protein (MOMP), Hepatitis B virus (HBV) surface antigen (HBsAg) or core antigen, Hepatitis C virus (HCV) antigens, Hepatitis Delta virus (HDV) antigens, Cytomegalovirus (CMV) antigens such as gp55, gB, and gH, Hepatitis A virus (HAV) antigens, malarial circumsporozoite antigens, and the like; and other proteins including structural proteins, binding proteins and peptides (for example, proteins of the MHC), and enzymes, such as β-galactosidase, alkaline phosphatase, and the like. In the case of antigens, the structural gene may alternatively encode one or more fragments of the antigen which bear epitopes specific to the pathogen from which they are derived. Similarly, membrane-bound proteins (including antigens, enzymes, and structural proteins) may be expressed in truncated and/or soluble form, by deleting the portion of the structural gene encoding membrane anchor region of the protein.

The expression systems useful in the invention comprise promoters derived from appropriate eukaryotic genes. Particularly preferred promoters are those found in yeast for synthesis of glycolytic enzymes, including those for 3-phosphoglycerate kinase (Hitzeman et al., *J. Bio. Chem.* (1980) 255:2073), and especially glyceraldehyde 3-phosphate dehydrogenase (GAPDH) (Travis et al., *J. Biol. Chem.* (1985) 260:4384–89). Other promoters include those from the enolase gene (M. J. Holland et al., *J. Biol. Chem.* (1981) 256:1385), the LEU2 gene obtained from YEp13 (J. Broach et al., *Gene* (1978) 8:121), and regulatable and hybrid promoters (J. Shuster, (1990) in Yeast Genetic Engineering (Barr, P. J., Brake, A. J., and Valenzuela, P., eds.) Butterworths, Stoneham, Ma., pp 83–108). It is presently preferred to express proteins fused to a suitable secretion leader, such as the yeast α-factor leader, the chicken lysozyme leader, the human tPA secretion leader, and the like. The α-factor leader is particularly preferred.

Cloning Methods

Site specific DNA cleavage is performed by treatment with a suitable restriction enzyme (or enzymes) under conditions which are generally understood in the art, generally following the manufacturer's directions. See, e.g., New England Biolabs, Product Catalog. In general, about 1 µg of plasmid or DNA sequence is cleaved by one unit of enzyme in about 20 µL of buffer solution; in the examples herein, typically, an excess of restriction enzyme is used to insure complete digestion of the DNA substrate. Incubation times of about 1 hr to 2 hr at about 37° C. are workable, although variations can be tolerated. After each incubation, protein is removed by extraction with phenol/chloroform, and may be followed by diethyl ether extraction, and the nucleic acid recovered from aqueous fractions by ethanol precipitation. If desired, size separation of the cleaved fragments may be performed by polyacrylamide gel or agarose gel electrophoresis using standard techniques. A general description of size separations is found in *Meth. Enzymol.* (1980) 65:499–560.

Restriction cleaved fragments may be blunt ended by treating with the large fragment of *E. coli* DNA polymerase I (Klenow) in the presence of the four deoxyribonucleotide triphosphates (dNTPs) using incubation times of about 15 to 25 min at 20° to 25° C. in 50 mM Tris, pH 7.6, 50 mM NaCl, 6 mM MgCl$_2$, 6 mM DTT and 5–10 µM dNTPs. The Klenow fragment fills in at 5' sticky ends but chews back protruding 3' single strands, even though the four dNTPs are present. If desired, selective repair can be performed by supplying only 1–3 of the dNTPs, within the limitations dictated by the nature of the sticky ends. After treatment with Klenow fragment, the mixture is extracted with phenol/chloroform and ethanol precipitated. Treatment under appropriate conditions with S1 nuclease results in hydrolysis of any single-stranded portion.

Synthetic oligonucleotides can be prepared using commercially available automated oligonucleotide synthesizers. Kinasing of single strands prior to annealing or for labeling may be achieved using an excess, e.g., approximately 10 units of polynucleotide kinase to 0.1 nmole substrate in the presence of 50 mM Tris, pH 7.6, 10 mM MgCl$_2$, 5 mM DTT, 1–2 mM ATP, 1.7 pmoles $^{32}$P-ATP (2.9 mCi/mmole), 0.1 mM spermidine, and 0.1 mM EDTA.

Ligations may be performed in 15–30 µL volumes under the following standard conditions and temperatures: 20 mM Tris-HCl, pH 7.5, 10 mM MgCl$_2$, 10 mM DTT, 33 µg/mLBSA, 10 mM-50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 µg/mL total DNA concentrations (5–100 nM total end concentration). Intermolecular blunt end ligations (usually employing a 10–30× molar excess of linkers) can be performed at 1 µM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8–9 in approximately 10–150 mM Tris using about 1–10 unit of BAP per µg of vector at about 60° C. for about 1 hr. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis may be used. This can be conducted using a synthetic oligonucleotide primer complementary to a single-stranded phage DNA to be mutagenized except for limited mismatching, representing the desired mutation. Briefly, a synthetic oligonucleotide is used as a primer to direct synthesis of a strand complementary to the phage, and the resulting double-stranded DNA is transfected into phage-supporting host bacteria. Cultures of the transfected bacteria are plated in top agar, permitting plaque formation from single cells which harbor the phage.

Theoretically, 50% of the new plaques will contain the phage having the mutated form as a single strand; 50% will have the original sequence. DNAs from the resulting plaques are hybridized with kinased synthetic primer. In general, one may vary the temperature, ionic strength, and concentration of chaotropic agent(s) in the hybridization solution to obtain conditions under which substantially no probes will hybridize in the absence of an "exact match." For hybridization of probes to bound DNA, the empirical formula for calculating optimum temperature under standard conditions (0.9M NaCl) is $$T(°C.)=4(N_G+N_C)+2(N_A+N_T)-5°C.,$$

where $N_G$, $N_C$, $N_A$, and $N_T$ are the numbers of G, C, A, and T bases in the probe (J. Meinkoth et al., *Anal. BioChem.* (1984) 138:267–84). Plaques corresponding to DNA that hybridizes specifically with the probe are then picked, cultured, and the DNA recovered.

Transformations into yeast can be carried out according to the method of A. Hinnen et at., *Proc. Nat. Acad. Sci. USA* (1978) 75:1929–33, or H. Ito et al., *J. Bacteriol.* (1983) 153:163–68. After DNA is taken up by the host cell, the vector integrates into the yeast genome at one or more sites homologous to its targeting sequence. It is presently preferred to linearize the vector by cleaving it within the targeting sequence using a restriction endonuclease, as this procedure increases the efficiency of integration.

Following successful transformations, the number of integrated sequences may be increased by classical genetic techniques. As the individual cell clones can carry integrated vectors at different locations, a genetic cross between two appropriate strains followed by sporulation and recovery of segregants can result in a new yeast strain having the integrated sequences of both original parent strains. Continued cylces of this method with other integratively transformed strains can be used to furthur increase the copies of integrated plasmids in a yeast host strain. One may also amplify the integrated sequences by standard techniques, for example by treating the cells with increasing concentrations of copper ions (where a gene for copper resistance has been included in the integrating vector).

Verification of Construction

Correct ligations for plasmid construction may be confirmed by first transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the plasmid construction, as is understood in the art. Plasmids from the transformants are then prepared according to the method of D. B. Clewell et al., *Proc. Nat. Acad. Sci. USA* (1969)62:1159, optionally following chloramphenicol amplification (D. B. Clewell, *J. Bacteriol.* (1972) 110:667). Isolated DNA is analyzed by restriction mapping and/or sequenced by the dideoxy method of F. Sanger et al., *Proc. Nat. Acad. Sci. USA* (1977) 74:5463 as further described by Messing et al., *Nucl. Acids Res,* (1981) 9:309, or by the method of Maxam and Gilbert, *Meth. Enzymol.* (1980) 65:499.

C. EXAMPLES

The examples presented below are provided as a further guide to the practitioner of ordinary skill in the art, and are not to be construed as limiting the invention in any way.

EXAMPLE 1

(Integration of sCD4)

Plasmid pJS161 was constructed starting with the yeast 2 μm origin, LEU2, and pBR322 from plasmid yEP13 (J. R. Broach et al., *Gene* (1979) 8:121), CUP1 (M. Karin et al., *Proc. Nat. Acad. Sci. USA* (1984) 81:337), and a structural gene encoding the secretion signal from chicken lysozyme fused to a sequence encoding soluble human CD4 receptor under the transcriptional control of the yeast ADH2/GAPDH hybrid promoter (Cousens et al. (1987) *Gene* 61:265) and a yeast α-factor mRNA termination signal. A map of the construct is shown in FIG. 1. Plasmid pJS162 contains the same components, but has CUP1 in the opposite orientation. The Xho1 site in the plasmid is within a DELTA element, and effectively divides the region into 5' and 3' targeting sequences.

Plasmids pJS161 and pJS162 were digested with Xho1 and used to transform yeast host strain AB110 (a leu2 mutant), selecting on leucine-deficient plates. The plates of Leu+(integrative) tranformants were replica-plated onto plates composed of YEPD+10 mM $CuSO_4$ to select for transformants having multiple copies of the plasmid. $Leu^+Cu^R$ colonies were purified by restreaking onto non-selective YEPD plates and tested for the expression of CD4. The results showed that strains isolated in this manner produced as much or more CD4 than similar yeast host strains containing the same CD4 expression cassette on an autonomously replicating plasmid (data not shown).

EXAMPLE 2

(Expression of Human Insulin-like Growth Factor-1)

Figure 2:
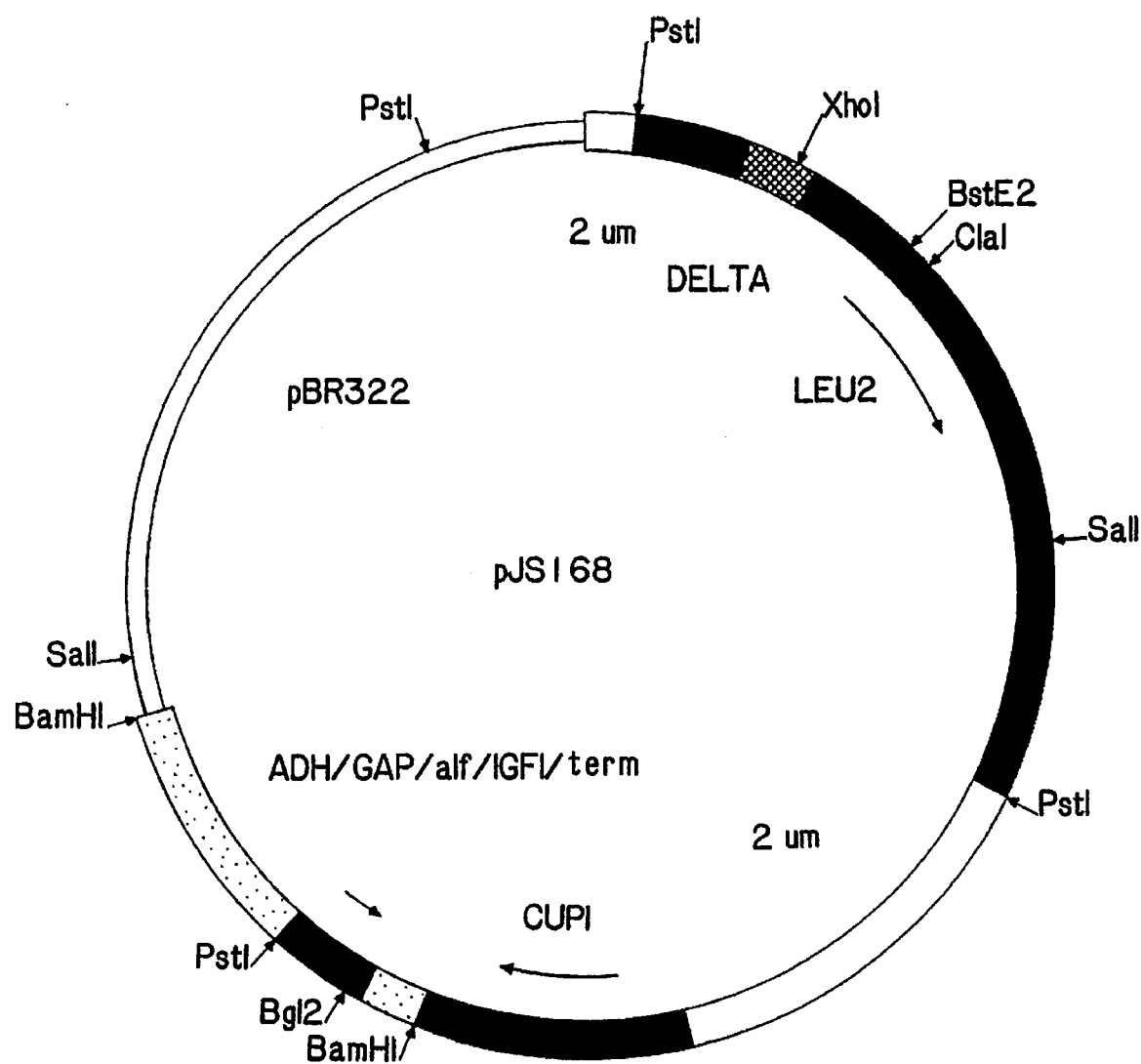
FIG. 2 depicts a map of plasmid pJS168.

(A) Plasmid pJS168 was constructed using the yeast 2 μm origin LEU2, pBR322, CUP1, and a structural gene encoding the yeast α-factor secretion leader fused to a sequence encoding human insulin-like growth factor-1 (IGF-I), under the transcriptional control of the yeast ADH2/GAPDH hybrid promoter and a yeast α-factor mRNA termination signal. A map of the construct is shown in FIG. 2.

Plasmid pJS168 was digested with Xho1 and used to transform strain DLM300 (a leu2 mutant), selecting on leucine-deficient plates. As a control, the same plasmid was cut with BstE2, which linearizes the plasmid in the LEU2 sequence (but not within the DELTA element) and used to transform strain DLM300 to leucine prototrophy. Thus, the control transformation should target integration to the yeast leu2 locus.

$Leu^+$transformants were picked and the DNA analyzed by Southern blotting for the position of the integration of the plasmid in the genome. In 5 of 7 DELTA-targeted transformants, the plasmid was integrated at a site other than the leu2 locus in the genome, one integrated at the leu2 locus, and one appeared to be a gene conversion from leu2 to LEU2 without any plasmid integration. For the control BstE2-cut plasmids, 3 of 7 transformants had plasmids integrated at the leu2 site, 3 had apparently undergone gene conversion without integration, and one had a plasmid integrated at a site other than leu2. Thus, vectors cleaved within the DELTA sequence were targeted to different areas of the genome.

Figure 3:
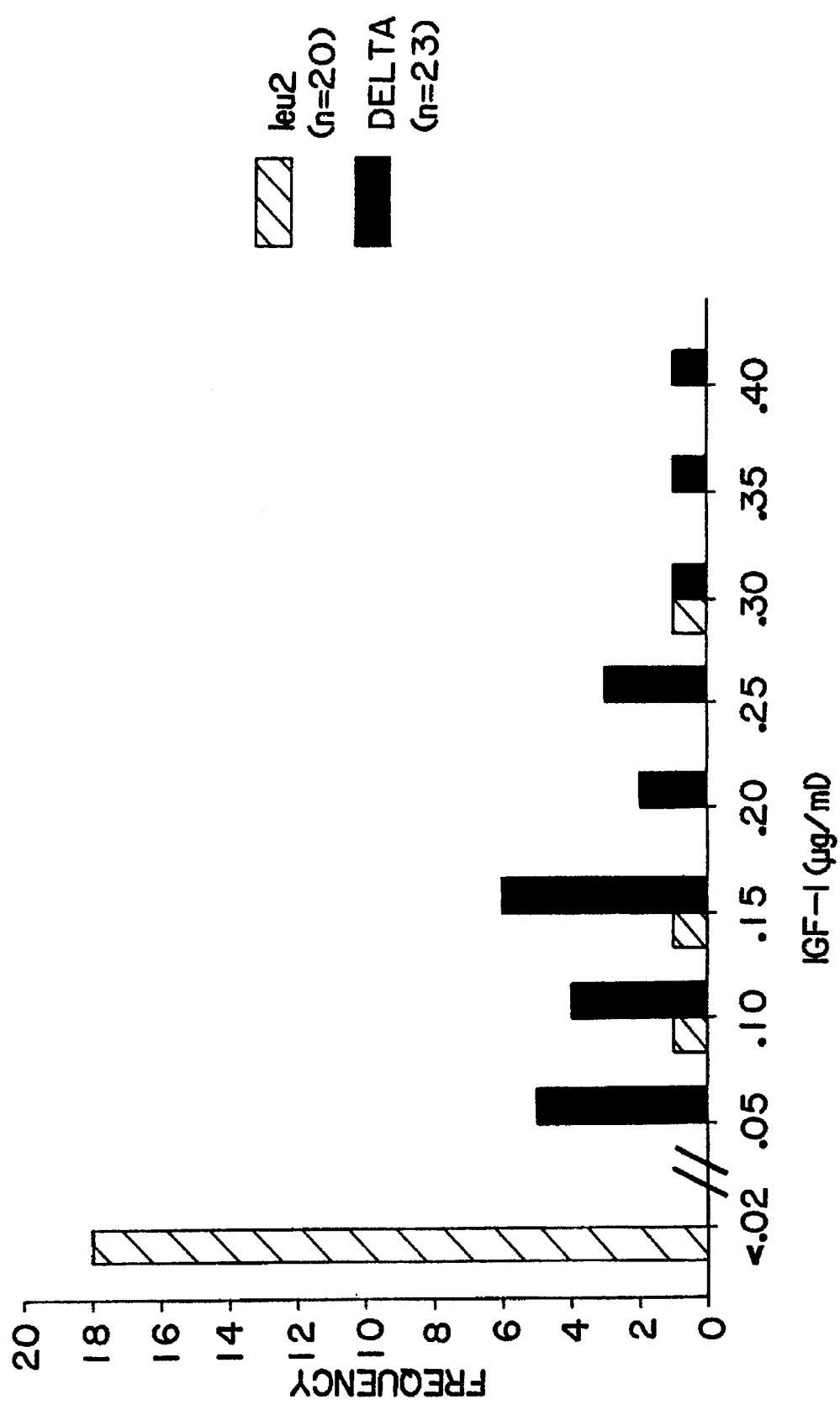
FIG. 3 depicts a comparison of IGF-I production levels for copper resistant transformants of pJS168 directed to either leu2 or DELTA sequences.

(B) The yeast colony plates obtained in part A above were then replica-plated to YEPD plates containing 10 mM $CuSO_4$. A total of 23 $Leu^+Cu^R$ colonies from the DELTA-targeted and 20 $Leu^+Cu^R$ colonies from the LEU2-targeted transformants were assayed for IGF-I production. The results demonstrated higher levels of IGF-I expression from DELTA-targeted transformants than from the control LEU2-targeted transformants (FIG. 3). Therefore, allowing for integration at dispersed repetitive sequences results in transformants diplaying higher levels of heterologous gene expression than is observed in transformants created by targeting with the LEU2 gene.

EXAMPLE 3

(Expression of β-Galactosidase)

Figure 4:
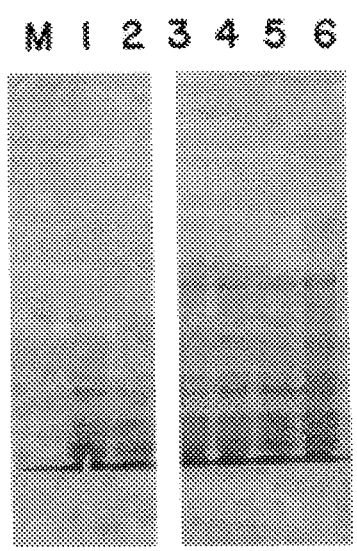
FIG. 4 is a photocopy of a gel depicting PAGE analysis of the expression of *E. coli* β-galactosidase in yeast transformed with pJS176 targeted at the DELTA sequences.
Figure 5:
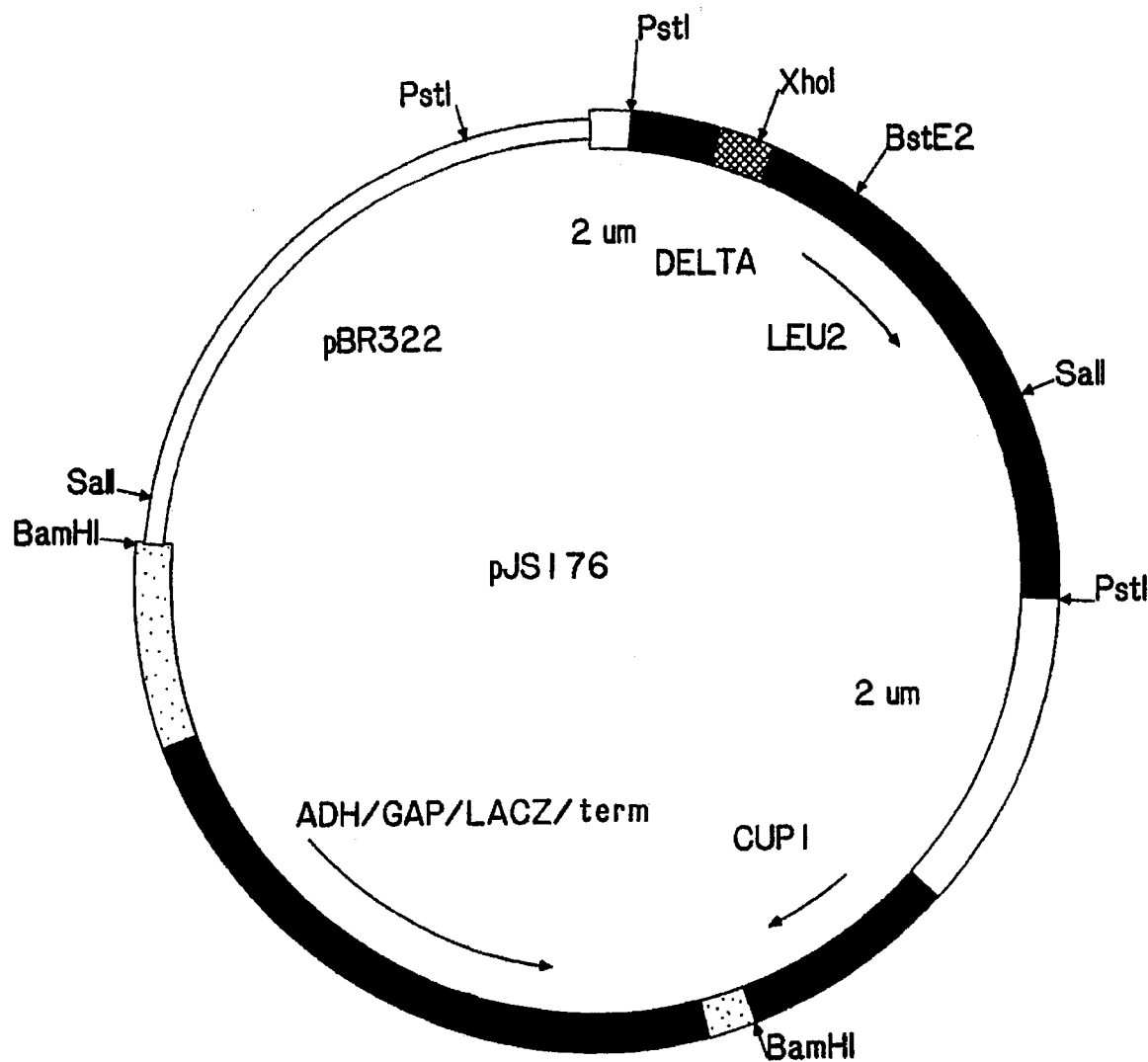
FIG. 5 depicts a map of plasmid pJS176.

Expression of a non-secreted protein using the vectors of the invention was demonstrated using *E. coli* β-galactosidase. An expression cassette consisting of an *E. coli* derived β-galactosidase gene between an ADH2/GAPDH promoter and a GAPDH mRNA terminator was cloned into the BamHI site in plasmid pJS168, replacing the IGF-I expression cassette. The resulting plasmid was linearized with Xho1 and used to transform yeast host strain AB110 to leucine prototrophy. The transformants were replica-plated onto a YEPD+10 mM $CuSO_4$ medium, and copper resistant colonies were obtained. The cells were grown in YEP +3% glycerol, washed with water, and broken with glass beads. The soluble extracted proteins were analyzed by SDS-polyacrylamide gel electrophoresis for β-galactosidase. Substantial levels of β-galactosidase were observed in the copper resistant transformants. FIG. 4 shows a photocopy of the SDS-PAGE gel. Lane M=molecular weight markers; Lane 1=AB110 control ($Leu^-$); Lane 2=single-copy integrant ($Leu^+$,Cu sensitive); Lanes 3–6= multiple-copy integrants ($Leu^+$,Cu resistant). Lanes 3–6 exhibited heavy bands corresponding to β-galactosidase expression, while Lane 2 exhibited a very light band at the corresponding position, and Lane 1 failed to exhibit a detectable band. A map of the integrative plasmid, pJS176, containing the β-galactosidase gene is depicted in FIG. 5. This plasmid provides a convenient vehicle, as the BamHI cassette may be removed easily and replaced with any desired expression cassette.

Deposit

Plasmid pJS176 was deposited in *E. coli* strain DH5α with the American Type Culture Collection (12301 Parklawn Dr., Rockville, Md.) on 18 Jul. 1990 under Accession number 68368. This deposit will be maintained under the provisions of the Budapest Treaty. All restriction of access to the deposit are removed upon issuance of this patent. This deposit is provided merely as a convenience to practitioners in the art, and is not an admission that a deposit is required under 35 USC §112. The sequence of the polynucleotides contained in the deposited material, as well as the amino acid sequence of the polypeptides encoded thereby, are incorporated herein by reference and are controlling in the event of any inconsistency with the sequences described herein. A license may be required to make, use or sell the deposited material, and no such license is hereby granted.

What is claimed is:

1. A vector for introducing multiple copies of heterologous DNA into a yeast host cell genome, wherein said yeast host cell genome comprises a plurality of DELTA sequences, each of said DELTA sequences being homologous to the DELTA sequence occurring in plasmid pJS176 (ATCC Accession Number 68368), and wherein said vector comprises:

a linear DNA molecule comprising first and second DNA sequences, wherein the first and second DNA sequences are homologous to the 5' end and 3' end, respectively, of each of the DELTA sequences in the host cell genome, whereby said vector is capable of homologous recombination with the host; and heterologous DNA flanked by said first and second DNA sequences.

2. The vector of claim 1, wherein said heterologous DNA comprises structural DNA in operable association with a promoter sequence and a terminator sequence functional in said host cell.

3. The vector of claim 2, wherein said heterologous DNA further comprises a selectable marker.

4. The vector of claim 3, wherein said selectable marker is selected from the group consisting of CUP1 and LEU2.

5. The vector of claim 2, wherein said structural DNA encodes truncated active human CD4, human insulin-like growth factor-I, or E. coli β-galactosidase.

6. A circular vector for introducing multiple copies of heterologous DNA into a yeast host cell genome, wherein said yeast host cell genome comprises a plurality of DELTA sequences, each of said DELTA sequences being homologous to the DELTA sequence occurring in plasmid pJS176 (ATCC Accession Number 68368), and wherein said vector comprises:

a circular DNA molecule comprising first and second DNA sequences, wherein the first and second DNA sequences are homologous to the 5' end and 3' end, respectively, of each of the DELTA sequences in the host cell genome, whereby said vector is capable of homologous recombination with the host; and heterologous DNA flanked on the 5' side by said first DNA sequence, and on the 3' side by said second DNA sequence;

wherein said circular DNA molecule has a unique restriction endonuclease recognition site positioned 5' of said first DNA sequence and 3' of said second DNA sequence.

7. The vector of claim 6, wherein said heterologous DNA comprises structural DNA in operable association with a promoter sequence and a terminator sequence functional in said host cell.

8. The vector of claim 7, wherein said heterologous DNA further comprises a selectable marker.

9. The vector of claim 8, wherein said selectable marker is selected from the group consisting of CUP1 and LEU2.

10. The vector of claim 7, wherein said structural DNA encodes truncated active human CD4, human insulin-like growth factor-I, or E. coli β-galactosidase.

11. A method for introducing multiple copies of heterologous DNA into a yeast host cell genome, wherein said yeast host cell genome comprises a plurality of DELTA sequences, each of said DELTA sequences being homologous to the DELTA sequence occurring in plasmid pJS176 (ATCC Accession Number 68368), wherein said method comprises:

providing a linear DNA molecule comprising first and second DNA sequences, wherein the first and second DNA sequences are homologous to the 5' end and 3' end, respectively, of each of the DELTA sequences in the host cell genome, whereby said linear DNA molecule is capable of homologous recombination with the host, and heterologous DNA flanked by said first and second DNA sequences; and transforming a suitable yeast host cell with said linear DNA, wherein said linear DNA undergoes homologous recombination with a plurality of DELTA sequences in the host genome.

12. The method of claim 11, wherein said heterologous DNA comprises structural DNA in operable association with a promoter sequence and a terminator sequence functional in said host cell.

13. The method of claim 12, wherein said heterologous DNA further comprises a selectable marker.

14. The method of claim 13 wherein said selectable marker is selected from the group consisting of CUP1 and LEU2.

15. The method of claim 12, wherein said structural DNA encodes truncated active human CD4, human insulin-like growth factor-1, or E. coli β-galactosidase.

16. A method for introducing multiple copies of heterologous DNA into a yeast host cell genome, wherein said yeast host cell genome comprises a plurality of DELTA sequences, each of said DELTA sequences being homologous to the DELTA sequence occurring in plasmid pJS176 (ATCC Accession Number 68368), wherein said method comprises:

providing a circular DNA molecule comprising first and second DNA sequences, wherein the first and second DNA sequences are homologous to the 5' end and 3' end, respectively, of each of the DELTA sequences in the host cell genome, whereby said circular DNA molecule is capable of homologous recombination with the host, and heterologous DNA flanked on the 5' side by said first DNA sequence, and on the 3' side by said second DNA sequence, wherein said circular DNA molecule has a unique restriction endonuclease recognition site positioned 5' of said first sequence and 3' of said second sequence;

cleaving said circular DNA molecule at said unique restriction site; and transforming a suitable yeast host cell with said cleaved DNA molecule, wherein said cleaved DNA undergoes homologous recombination with a plurality of DELTA sequences in the host genome.

17. The method of claim 16, wherein said heterologous DNA comprises structural DNA in operable association with a promoter sequence and a terminator sequence functional in said host cell.

18. The method of claim 17, wherein said heterologous DNA further comprises a selectable marker.

19. The method of claim 18, wherein said selectable marker is selected from the group consisting of CUP1 and LEU2.

20. The method of claim 17, wherein said structural DNA encodes truncated active human CD4, human insulin-like growth factor-1, or E. coli β-galactosidase.

* * * * *